United States Patent
Maniscalco

(10) Patent No.: US 7,078,022 B2
(45) Date of Patent: Jul. 18, 2006

(54) SUNSCREEN COMPOSITIONS AND METHODS OF USE THEREOF

(75) Inventor: Thomas J. Maniscalco, Danbury, CT (US)

(73) Assignee: Avon Products, Inc., New York, NY (US)

(*) Notice: Subject to any disclaimer, the term of this patent is extended or adjusted under 35 U.S.C. 154(b) by 192 days.

(21) Appl. No.: 10/805,757

(22) Filed: Mar. 22, 2004

(65) Prior Publication Data

US 2005/0063924 A1      Mar. 24, 2005

Related U.S. Application Data

(63) Continuation of application No. 10/444,332, filed on May 22, 2003, now abandoned.

(60) Provisional application No. 60/383,077, filed on May 23, 2002.

(51) Int. Cl.
*A61Q 17/04*   (2006.01)
*A61Q 19/00*   (2006.01)
*A61Q 19/04*   (2006.01)
*A61K 8/00*    (2006.01)
*A61K 8/02*    (2006.01)

(52) U.S. Cl. .................. 424/59; 424/60; 424/400; 424/401

(58) Field of Classification Search .............. 424/59, 424/60, 400, 401
See application file for complete search history.

(56) References Cited

U.S. PATENT DOCUMENTS 5,656,261 A    8/1997    Cerami et al. ............ 424/53
5,853,703 A   12/1998    Cerami et al. ............ 424/53

FOREIGN PATENT DOCUMENTS

WO          WO 02/07725 A1    1/2002

OTHER PUBLICATIONS

International Search Report for PCT/US3/16477, mailing date: Nov. 27, 2003.

*Primary Examiner*—Shelley A. Dodson
(74) *Attorney, Agent, or Firm*—Mintz, Levin, Cohn, Ferris, Glovsky and Popeo, P.C.; Ivor R. Elrifi; Matthew Pavao

(57) ABSTRACT

Disclosed herein are novel methods for reducing or preventing the harmful effects of solar radiation on skin. Also disclosed are novel sunscreen compositions comprising 3-[2-(4-diethylaminophenyl)-2-oxoethyl]thiazolium salt for reducing or preventing the harmful effects of solar radiation on skin. Agents that provide UV-A and UV-B filters are also included. The invention further discloses additional sunscreen active agents, emollients, humectants, dry-feel modifiers, waterproofing agents, insect repellants, antimicrobial preservatives, antioxidants, chelating agents, fragrances and moisturizers, suitable carriers for topical application and emulsions.

20 Claims, 1 Drawing Sheet

SUNSCREEN COMPOSITIONS AND METHODS OF USE THEREOF

RELATED APPLICATIONS

This application is a continuation of U.S. Ser. No. 10/444,332, filed May 22, 2003, now abandoned which claims the benefit of U.S. Ser. No. 60/383,077, filed May 23, 2002, each of which is incorporated herein by reference in its entirety.

FIELD OF THE INVENTION

This invention relates generally to methods and compositions for reducing or preventing the harmful effects of solar radiation on skin.

BACKGROUND OF THE INVENTION

A wide variety of compositions are known in the art for providing cosmetic and/or pharmacologic benefits to human skin. Benefits sought include, for example, prevention, treatment or amelioration of environmental or age-related damage or deterioration of the skin, improved appearance by modifying surface characteristics, improved feel by moisturizing, and prevention or treatment of specific skin disorders.

It is now generally recognized that exposure to solar radiation can have adverse health consequences, sometimes not appearing until several years following the exposure. Of course, the immediately appearing "sunburn" from an overexposure can itself be a serious acute health problem.

Products are available to reduce the amount of solar ultraviolet radiation received by the skin during exposure to the sun's rays. Typical product formulations are lotions, creams, ointments, or gels containing chemical and/or physical barriers to ultraviolet transmission. These vary considerably in their abilities to protect the skin against the physical and biochemical effects of ultraviolet radiation.

Earlier sunscreening formulations were designed to protect against sunburn from a limited solar exposure period, while transmitting sufficient radiation to permit skin tanning. However, the current focus is on eliminating as much ultraviolet exposure as possible, it being recognized that skin tanning, while esthetically pleasing to some, is a clear indication of tissue damage from overexposure to solar radiation. It has been recently discovered that any amount of unprotected exposure can potentially cause immune system suppression and lead to future health problems, such as skin carcinomas and other dermatological disorders.

SUMMARY OF THE INVENTION

In one embodiment, the present invention includes a method of reducing or preventing harmful effects of solar radiation on skin by applying a composition which includes an effective amount of 3-[2-(4-diethylaminophenyl)-2-oxoethyl]thiazolium salt.

In another embodiment, the method includes a composition which includes an effective amount of 3-[2-(4-diethylaminophenyl)-2-oxoethyl]thiazolium salt which is between about 0.5% and about 10% by weight of the composition.

In another embodiment, the method further includes a suitable carrier for topical application to human skin.

In another embodiment, the method includes an effective amount of the compound of the invention which is between about 0.5% and about 10% by weight of the composition.

In another embodiment, the method includes one or more agents that provide a UV-B filter. Such agents include paramethoxycinnamic acid esters and octyl salicylate.

In another embodiment, the method further includes one or more agents that provide a UV-A filter. Such agents dibenzoylmethane derivatives, 4-(1,1-dimethylethyl)-4'-methoxydibenzoylmethane, and 4-isopropyl dibenzoylmethane.

In a preferred embodiment, the present invention includes a sunscreen composition for the reduction or prevention of harmful effects of solar radiation on skin. The sunscreen composition includes one or more agents that provide a UV-B filter and an effective amount of a compound of the formula I and a suitable carrier for application to the skin.

In another embodiment, the sunscreen composition includes an effective amount of the compound of the invention which is between about 0.5% and about 10% by weight of the composition.

In another embodiment, the sunscreen composition includes one or more agents that provide a UV-B filter. Such agents include paramethoxycinnamic acid esters and octyl salicylate.

In another embodiment, the sunscreen composition further includes one or more agents that provide a UV-A filter. Such agents include dibenzoylmethane derivatives, 4-(1,1-dimethylethyl)-4'-methoxydibenzoylmethane, and 4-isopropyl dibenzoylmethane.

In another embodiment, the sunscreen composition further includes one or more sunscreen active agents. Such sunscreen active agents include para aminobenzoic acid, avobenzone, cinoxate, dioxybenzone, homosalate, menthyl anthranilate, octocrylene, octyl methoxycinnamate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, homomenthyl salicylate, Benzophenone-3, Uvinul MS-40, Uvasorb MET/C, and Neo Heliopan 303 or mixtures thereof.

In another embodiment, the sunscreen composition includes one or more additional components. Such additional components include emollients, humectants, dry-feel modifiers, waterproofing agents, insect repellants, antimicrobial preservatives, antioxidants, chelating agents, fragrances and moisturizers.

In another embodiment, the sunscreen composition is in the form of an emulsion. The emulsion can further include a hydrophobic component that imparts film-forming and waterproofing characteristics to the emulsion. The hydrophobic component can be a polymer. The polymer can include, for example, a polyanhydride resin, or a copolymer, such as one derived of octadecene-1 and maleic anhydride monomers, or a copolymer vinyl pyrollidone and eicosene monomers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
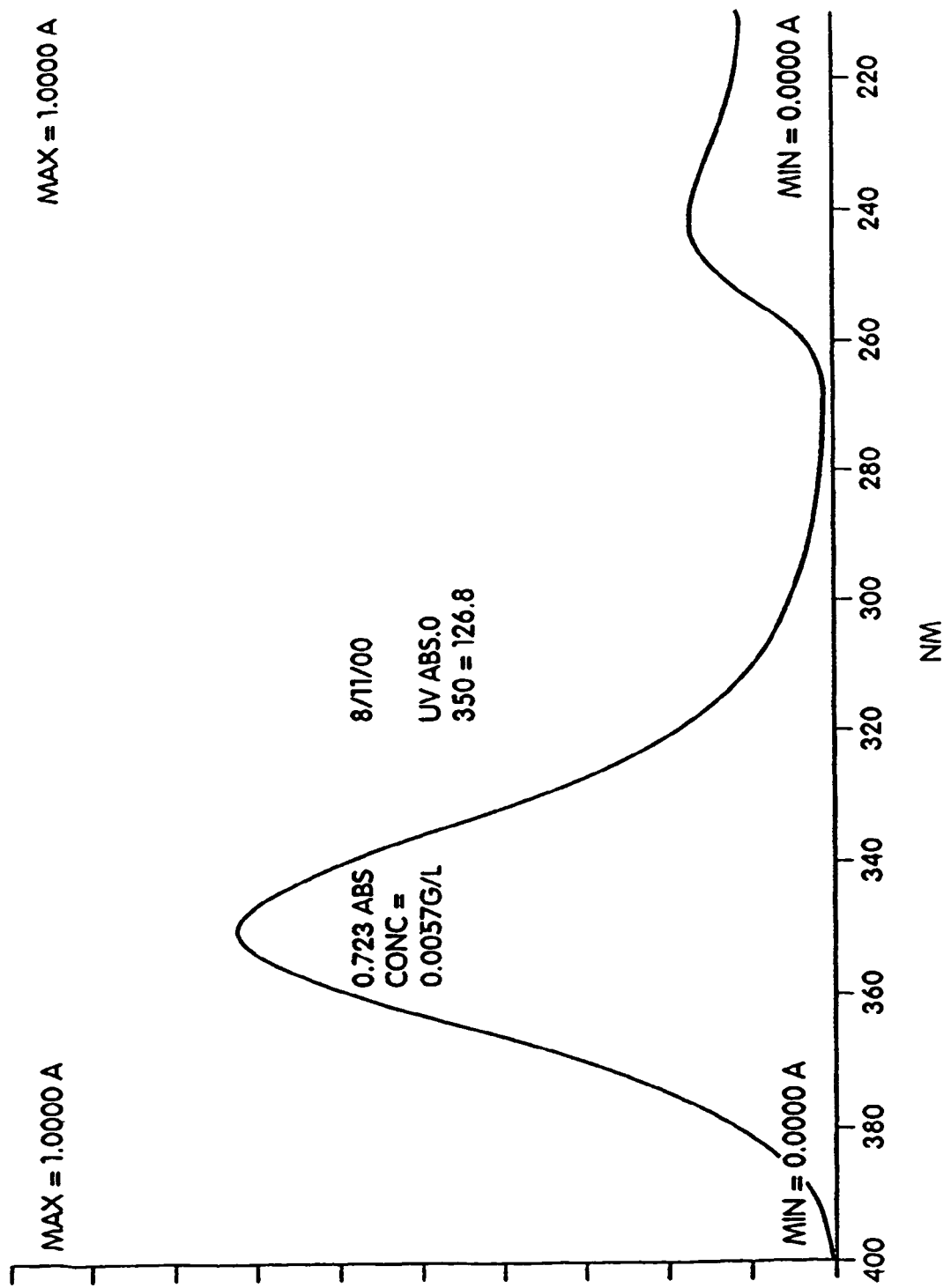
FIG. 1 is a Ultraviolet (UV) spectrum showing the UV absorbance of 3-[2-(4-diethylaminophenyl)-2-oxoethyl] thiazolium salt.

The present invention is directed to a composition for a sunscreen designed for topical application to human skin. More particularly, the present invention is directed to the use of 3-[2-(4-diethylaminophenyl)-2-oxoethyl]thiazolium salt to protect skin against harmful UV radiation.

Typical sunscreen compositions include organic or inorganic compounds which reduce the ultraviolet radiation that reaches the skin by scattering or absorbing ultraviolet rays. Commercial formulations are usually in the form of a lotion to be spread over the exposed skin. These lotions usually contain more than one active agents, and are designed to protect skin against various wavelengths of light. In addition, commercial formulations frequently contain further components which provide other desirable properties, such as fragrance and/or moisturizers, such as aloe vera.

Many conventional cosmetic cream and lotion compositions are described, for example, in Sagarin, Cosmetics Science and Technology, 2nd Edition, Volume 1, Wiley Interscience (1972), and Encyclopedia of Chemical Technology, Third Edition, Volume 7.

Ultraviolet (UV) radiation with a wavelength of approximately 290–400 nanometers (nm) has long been known to have harmful effects on human skin. There is an increasing awareness of the need to use sunscreens in order to protect exposed skin. UV-B radiation is produced between 290–320 nm and UV-A radiation between 320–400 nm. UV-C radiation, which is generally defined as radiation with a wavelength of less than approximately 290 nm, is absorbed by the atmosphere and is therefore not considered to be of general concern.

UV radiation damage to human skin may result in damage to the dermal infrastructure which, in its most extreme form, may result in malignancies. UV radiation falling within the range of 290–320 nm may cause erythema and edema associated with sunburn. A sunscreen composition should include both UV-A and UV-B filters to prevent most of the sunlight within the full range of about 280 nm to about 400 nm from damaging human skin.

Sunscreen Active Agents:

The term "sunscreen active agent" shall be used herein to include all of those materials, used singly or in combination, that are regarded as acceptable for use as active sunscreening ingredients.

In preferred embodiments, the present invention is a formulation for a sunscreen comprising an effective amount of 3-[2-(4-diethylaminophenyl)-2-oxoethyl]thiazolium salt:

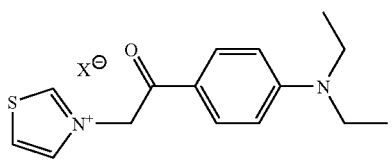

3-[2-(4-diethylaminophenyl)-2-oxoethyl]thiazolium salt wherein X— is a pharmaceutically acceptable anion, such as chloride, bromide, tosylate, mesylate, mesitylene, sulfonate, and the like.

3-[2-(4-diethylaminophenyl)-2-oxoethyl]thiazolium salt is shown to improve the elasticity and reduce the wrinkling of skin. It has been found to have the unexpected benefit of acting as an excellent UV absorber, particularly in the UV-A range. FIG. 1 provides the UV spectrum for 3-[2-(4-diethylaminophenyl)-2-oxoethyl]thiazolium salt. It clearly demonstrates the UV absorbing properties of the compound. The maximum UV absorption occurs at a wavelength of 350 nm.

The preferred compositions of the present invention comprise an effective amount of 3-[2-(4-diethylaminophenyl)-2-oxoethyl]thiazolium salt. As used herein, the term "effective amount" means that amount of the compound that will elicit the biological or medical response of a tissue, system animal or human that is being sought by a researcher or clinician. Thus, an effective amount of a sunscreen active agent of the invention is that amount of the compound which is sufficient to provide the appropriate degree of protection from the sun. The compositions preferably include about 0.5% of 3-[2-(4-diethylaminophenyl)-2-oxoethyl]thiazolium salt by weight of the composition to about 10% of 3-[2-(4-diethylaminophenyl)-2-oxoethyl]thiazolium salt by weight of the composition. A preferable range is between about 0.5% and about 10% of 3-[2-(4-diethylaminophenyl)-2-oxoethyl]thiazolium salt by weight of the composition. The term "percent by weight" as used herein means the percent by weight of the ingredient per weight of the overall formulation.

The composition preferably also comprises a suitable carrier for topical application to human skin and one or more sunscreen active agents, such as those that provide a UV-B filter and, in some embodiments, additionally a UV-A filter.

Examples of UV-B filters that are incorporated into the composition in some embodiments of the present invention include paramethoxycinnamic acid esters, such as 2-ethylhexyl paramethoxycinnamate, commonly referred to as octyl methoxycinnamate or PARSOL MCX, having an ethyl group extending from the 2 position of the hexyl long chain backbone:

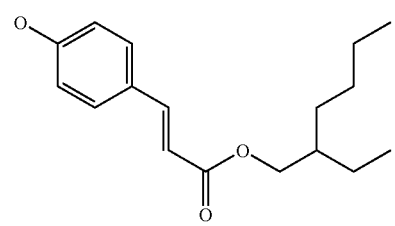

2-ethylhexyl paramethoxycinnamate, PARSOL MCX, octyl methoxycinnamate and octyl salicylate:

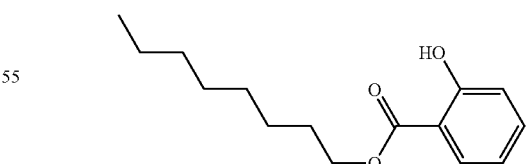

octyl salicylate

In some embodiments the composition may also include further UV-A filters. Examples of UV-A filters are the dibenzoylmethane derivatives, particularly 4-(1,1-dimethylethyl)4'-methoxydibenzoylmethane (PARSOL 1789):

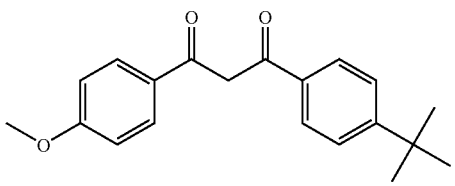

4-(1,1-dimethylethyl)-4'-methoxydibenzoylmethane
PARSOL 1789 and 4-isopropyl dibenzoylmethane (EUSOLEX 8020):

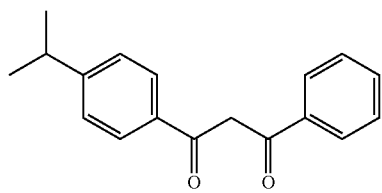

4-isopropyl dibenzoylmethane, EUSOLEX 8020

In additional embodiments, sunscreen active agents include, but are not limited to, para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum.

In further embodiments, sunscreen active agents include homomenthyl salicylate available under the trade name Uniderm Homsal from Universal Preserv-A-Chem; Benzophenone-3, available under the trade name Escalol 567 from ISP VanDyk, Uvinul MS-40 from BASF, and Uvasorb MET/C from 3V Inc.; Octyl Salicylate, available under the trade name Neo Heliopan OS from Haarmann & Reimer; Octocrylene, available under the trade name Uvinul N-539-SG from BASF, and the trade name Neo Heliopan 303 from Haarmann & Reimer; or mixtures thereof.

In a preferred embodiment, combinations of two or more sunscreen ingredients are used in a formulation to achieve higher levels of ultraviolet absorption or to provide useful absorption over a wider range of ultraviolet wavelengths than can be attained with a single active component.

Compositions of 3-[2-(4-diethylaminophenyl)-2-oxoethyl]thiazolium salt may be produced by methods found in U.S. Pat. Nos. 5,656,261 and 5,853,703, and in WO 02/07725, each of which is incorporated herein by reference.

The compounds of the invention are, in some embodiments of the present invention, combined with known moisturizers, emollients, solvents, lubricants, emulsifiers and/or other common cosmetic formulation ingredients which may enhance the solubility of the compound, produce emulsification, provide thickening, and/or provide other skin enhancement properties known in the art. The preferred embodiments of the present invention can be produced as a lotion, as a gel, in solid stick form, as an emulsion, as an aerosol, and in other forms.

Emulsions/Emulsifiers:

In some preferred embodiments of the present invention, the composition is in the form of an emulsion. In a preferred embodiment this emulsion comprises a hydrophobic component which imparts film forming and waterproofing characteristics to the emulsion. Examples of such hydrophobic components are copolymers derived of octadecene-1 and maleic anhydride, polyanhydride resin and a copolymer of vinyl pyrrolidone and eicosene monomers.

A stable emulsion is a mixture of two immiscible liquids, i.e. liquids that are not mutually soluble, but which can form a fluid in which very small droplets of one component are stably dispersed throughout the other liquid, giving the mixture the appearance of a homogeneous fluid. Emulsions can include particulate materials and materials which are solid or solid-like at room temperature, but which will liquefy at higher temperatures used during formation of the emulsion. The presence of an emulsifier enhances the ability of one of the immiscible liquids to remain in a continuous form, while allowing the other immiscible liquid to remain in a dispersed droplet form. Thus, one function of an emulsifier, a stabilizing compound, is to assist in the production of a stable emulsion. A secondary function of emulsifiers is to provide a thickening or "bodying" to an emulsion. Typically, emulsifiers are molecules with non-polar and polar parts that are able to reside at the interface of the two immiscible liquids.

The term "emulsion" shall be used herein to identify oil-in-water (o/w) or water-in-oil (w/o) type dispersion formulations intended for application to the skin, particularly lotions and creams providing cosmetic or therapeutic benefits. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers, sunless tanning agents and the like, depending on the intended uses for the formulations.

Techniques for forming o/w and w/o emulsions are very well known in the art. The present invention is not dependent upon any particular formulation technique, it being recognized that the choice of specific formulation components may well make necessary some specific formulation procedure.

Suitable emulsifiers for one aspect of the invention are those known in the art for producing oil-in-water and/or water-in-oil type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase, and assists with both the formation and the maintenance, or stability, of the emulsion. Suitable emulsifiers for another aspect of the invention are those known in the art for producing water-in-oil type emulsions. The typical water-in-oil emulsifier has a HLB value of about 4 to about 6, as is well known in the art; however, this "rule" is also known to have numerous exceptions. Selection of suitable water-in-oil emulsifiers is well known in the formulation art.

Most of the widely used emulsifier systems for sunscreen formulations can be used in the invention. Particularly preferred emulsifiers are PEG-8 Distearate available under the trade name of Emerest 2712 from Henkel, PEG-5 Glyceryl Stearate available under the trade name POEM-S-105 from Riken Vitamin Oil, PEG-6 Hydrogenated Castor Oil, available under the trade name Sabowax ELH6 from Sabo, PEG-6 Oleate, available under the trade name STEPAN PEG-300 MO from Stepan, Sorbitan Sesquioleate, available under the trade name Arlacel 83 and Arlacel C from ICI Surfactants, TEA-Stearate, available under the trade name of Cetasal from Gaftefosse S.A. Another preferred emulsifier is neutralized cetyl phosphate, available under the trade name Amphisol A from LaRoche. Most preferred is an Acrylate/$C_{10}$–$C_{30}$ alkyl acrylate cross polymer of $C_{10}$–$C_{30}$ alkyl acrylates and one or more monomers of acrylic acid, methacrylic acid or one of their simple esters crosslinked within allyl ether of sucrose or an allyl ether of pentaerythritol, available under the trade names of Pemulen TR from B.F. Goodrich. The amount of emulsifier used in the present invention is present in an amount of about 0.1 to about 10% by weight, preferably about 0.5 percent to about 5 percent by weight, most preferably about 2 percent to about 4 percent by weight. The choice of an emulsifier is well within ordinary skill in the art and is not a critical aspect of the invention. Additional preferred emulsifiers that may be employed include Sorbitan Triisostearate available under the trade name Crill 6 from Croda Oleochemicals, and Polyglyceryl-3 Distearate available under the trade name Cremophor GS 32 from BASF.

Water:

Water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or composition can range from about 15 to 95 weight percent, preferably from about 45 to 75 percent.

Moisturizers:

In addition to protecting the skin from exposure to solar radiation, the present invention also includes methods of treating the skin for conditions which might be associated with such exposure, e.g., dryness. In preferred embodiments the compositions of the present invention include moisturizers, such as guanidine, glycolic acid, glycolate salts such as ammonium and quaternary alkyl ammonium, lactic acid and lactate salts, aloe vera in any of its variety of forms, polyhydroxy alcohols such as sorbitol, glycerol, hexanetriol, propylene glycol, butylene glycol, hexylene glycol, polyethylene glycols, sugars and starches, sugar and starch derivatives, hyaluronic acid, lactamide monoethanolamine, acetamide monoethanolamine and mixtures thereof. Moisturizers and techniques for preparing moisturizers is well known in the art. For example, U.S. Pat. No. 4,454,159 concerns preparations for treating irritated, pruritic and dry skin which contain a combination of lipids/lipoids comprising glycerol trioleate and other glyceride oils of certain fatty acids, tocopherol, squalene, collagen protein, a humectant, and isopropyl palmitate. The present invention is not dependent upon any particular preparation or formulation technique.

Additional/Optional Components:

The compositions of the present invention may contain a wide range of additional, optional components. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, waterproofing agents, and viscosity increasing agents (aqueous and nonaqueous).

Emollients:

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$–$C_{15}$ Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Coming Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the present invention.

Humectants:

A humectant is a moistening agent that promotes retention of water due to its hygroscopic properties. Suitable humectants include glycerin, polymeric glycols such as poyethylene glycol and polypropylene glycol, mannitol and sorbitol. One or more humectants can optionally be included in the in the sunscreen in amounts from about 1 to 10 weight percent.

Dry-feel Modifier:

A dry-feel modifier is an agent which when added to an emulsion, imparts a "dry feel" to the skin when the emulsion dries. Dry feel modifiers can be used in addition to the epichlorohydrin cross-linked glyceryl starch used in the formulation of the present invention. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A.

Waterproofing Agents:

A waterproofing or water resistance agent is a hydrophobic material that imparts film forming and waterproofing characteristics to an emulsion. A suitable waterproofing agent is a copolymer of vinyl pyrollidone and eicosene and dodecane monomers such as Ganex V 220 and Ganex V 216 Polymers, respectively, trade names of ISP Inc. of Wayne, N.J. U.S.A. Still other suitable waterproofing agents include polyurethane polymer, such as Performa V 825 available from New Phase Technologies and polyanhydride resin No. 18 available under the trade name PA-18 from Chevron. The waterproofing agent is used in amounts effective to allow the sunscreen to remain effective on the skin after exposure to circulating water for at least 40 minutes for water resistance and at least 80 minutes for waterproofing using the procedures described by the U.S. Food and Drug Administration in "Sunscreen Drug Products for OTC Human Use," Federal Register, Vol. 43, Aug. 25, 1978, Part 2, pp. 38206–38269.

Insect Repellants:

Insect repelling components are desirable in sunscreening emulsions, since the emulsions are normally used primarily by persons engaged in outdoor activities. The most widely used active agent for personal care products is N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

Antimicrobial Preservative:

An antimicrobial preservative is a substance or preparation which destroys, or prevents or inhibits the proliferation of, microorganisms in the sunscreen composition, and which may also offer protection from oxidation. Preservatives are frequently used to make self-sterilizing, aqueous based products such as emulsions. This is done to prevent the development of microorganisms that may be in the product from growing during manufacturing and distribution of the product and during use by consumers, who may further inadvertently contaminate the products during normal use. Typical preservatives include the lower alkyl esters of para-hydroxybenzoates (parabens), especially methylparaben, propylparaben, isobutylparaben and mixtures thereof, benzyl alcohol, phenyl ethyl alcohol and benzoic acid. The preferred preservative is available under the trade name of Germaben II from Sutton. One or more antimicrobial preservatives can optionally be included in an amount ranging from about 0.001 to about 10 weight percent, preferably about 0.05 to about 1 percent.

Antioxidant:

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, Vitamin E and Vitamin C. One or more antioxidants can optionally be included in the sunscreen composition in an amount ranging from about 0.001 to about 5 weight percent, preferably about 0.01 to about 0.5 percent.

Chelating Agents:

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.2 weight percent preferably about 0.01% weight percent.

Fragrances:

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modem trend is to use synthetically prepared fragrances, particularly in high-volume products. The preferred fragrances for use in the present invention are Fragrance SZ-2108 and Fragrance SZ-1405 available from Sozio, Inc. One or more fragrances can optionally be included in the sunscreen composition in an amount ranging from about 0.001 to about 5 weight percent, preferably about 0.01 to about 0.5 percent by weight.

pH Modifier:

A pH modifier is a compound that will adjust the pH of a formulation to a lower, e.g., more acidic pH value, or to a higher, e.g., more basic pH value. The selection of a suitable pH modifier is well within the ordinary skill of one in the art.

Topical Administration:

In a preferred embodiment, the method comprises the topical administration of the compositions and formulation of the invention. "Topical application", "applied topically", "topical administration" and "administered topically", are used interchangeably to mean the process of applying or spreading one or more compositions according to the instant invention onto the surface of the skin of a subject in need thereof. Topical formulations may be comprised of oil-in-water and/or water-in-oil type emulsions but are not limited in this respect. Topical formulations contemplated by the present invention may include delayed release compositions capable of producing a slow release of the sunscreen active agent.

Elasticity and Facial Wrinkles

The compound of 3-[2-(4-diethylaminophenyl)-2-oxoethyl]thiazolium salt is shown to improve the elasticity and reduce the wrinkling of skin. The compositions should provide exceptional skin rejuvenation and moisturizing properties in comparison with typical prior art sunscreen compositions.

There are two different types of wrinkles, fine wrinkles and dynamic wrinkles. Traditionally, fine wrinkles are believed to result from aging, sun exposure, and reduction in collagen and elastic fibers of the skin. Deep wrinkles are associated with the build-up of the musculature below the skin surface. When people with healthy skin are making facial expressions, they show dynamic wrinkles around the facial expression muscles. When those muscles are at rest, skin resumes its most smoothness due to elasticity. It is believed, however, that muscles at resting stage are in a slight contractile posture due to base-level/spontaneous quantal release of acetylcholine. Healthy skin looks smooth because elasticity overcomes this mild contractile muscle posture to hide obvious wrinkles. Facial wrinkles are generated presumably by the breakdown of skin support of collagen and elastin fiber due to aging and sun exposure, diminished function of sweat glands and fat pad atrophy beneath the dermis. In addition, years of repeating the facial muscle contraction can thicken the muscle layer and thus deepen the wrinkles.

Many approaches are taken to reduce the appearance of facial wrinkles based on the understanding of the molecular basis of wrinkle formation. Such treatments include cosmetic products, drug therapy and surgical procedures. For example, many cosmetic products contain alpha hydroxy acids, which may stimulate collagen synthesis. Another common treatment utilizes retinol, a derivative of vitamin A, (or its stronger, prescribed version Retin-A and Renova) which helps collagen production. Antioxidants such as vitamin C and E and coenzyme Q-10 are believed to counteract free radicals, which damage cells and cause aging and have been used in treatments of wrinkles. Recently, the FDA approved cosmetic use of Botox (an extremely diluted form of botulinum toxin) to treat glabella frown lines.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims

We claim:

1. A method of reducing or preventing harmful effects of solar radiation on skin comprising, applying a composition, comprising an effective amount of 3-[2-(4-diethylaminophenyl)-2-oxoethyl]thiazolium salt.

2. The method of claim 1, wherein the effective amount of 3-[2-(4-diethylaminophenyl)-2-oxoethyl]thiazolium salt is between about 0.5% and about 10% by weight of the composition.

3. The method of claim 1, wherein the composition further comprises a suitable carrier for topical application to human skin.

4. The method of claim 1, wherein the composition further comprises one or more agents that provide a UV-B filter.

5. The method of claim 4, wherein the one or more agents that provide a UV-B filter are selected from the group consisting of paramethoxycinnamic acid esters and octyl salicylate.

6. The method of claim 1, wherein the composition further comprises one or more agents that provide a UV-A filter.

7. The method of claim 6, wherein the one or more agents that provide a UV-A filter are selected from the group consisting of dibenzoylmethane derivatives, 4-(1,1-dimethylethyl)-4'-methoxydibenzoylmethane, and 4-isopropyl dibenzoylmethane.

8. The method of claim 1, wherein the composition further comprises one or more agents that provide a UV-A filter and one or more agents that provide a UV-B filter.

9. A sunscreen composition for the reduction or prevention of harmful effects of solar radiation on skin comprising an effective amount of 3-[2-(4-diethylaminophenyl)-2-oxoethyl]thiazolium salt and a suitable carrier for application to the skin.

10. The composition of claim 9, wherein the effective amount of 3-[2-(4-diethylaminophenyl)-2-oxoethyl]thiazolium salt is between about 0.5% and about 10% by weight of the composition.

11. The composition of claim 9, wherein the composition further comprises one or more agents that provide a UV-B filter.

12. The composition of claim 11, wherein the one or more agents that provide a UV-B filter are selected from the group consisting of paramethoxycinnamic acid esters and octyl salicylate.

13. The composition of claim 9, wherein the composition further comprises one or more agents that provide a UV-A filter.

14. The composition of claim 13, wherein the one or more agents that provide a UV-A filter are selected from the group consisting of dibenzoylmethane derivatives, 4-(1,1-dimethylethyl)-4'-methoxydibenzoylmethane, and 4-isopropyl dibenzoylmethane.

15. The composition of claim 9, wherein the composition further comprises one or more agents that provide a UV-A filter and one or more agents that provide a UV-B filter.

16. The composition of claim 9, wherein the composition further comprises one or more sunscreen active agents, wherein the one or more sunscreen active agents are selected from the group consisting of para aminobenzoic acid, avobenzone, cinoxate, dioxybenzone, homosalate, menthyl anthranilate, octocrylene, octyl methoxycinnamate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, homomenthyl salicylate, Benzophenone-3, Uvinul MS-40, Uvasorb MET/C, and Neo Heliopan 303 or mixtures thereof.

17. The composition of claim 9, wherein the composition further comprises one or more components selected from the group consisting of emollients, humectants, dry-feel modifiers, waterproofing agents, insect repellants, antimicrobial preservatives, antioxidants, chelating agents, fragrances and moisturizers.

18. The composition of claim 9, wherein the composition is in the form of an emulsion.

19. The emulsion of claim 18, further comprising a hydrophobic component that imparts film-forming and waterproofing characteristics to the emulsion.

20. The emulsion of claim 19, wherein the hydrophobic component is a polymer selected from the group consisting of a copolymer comprising octadecene-1 and maleic anhydride monomers, polyanhydride resin and a copolymer comprising vinyl pyrollidone and eicosene monomers.

* * * * *